US00PP15145P2

(12) United States Plant Patent
Mowrey et al.

(10) Patent No.: US PP15,145 P2
(45) Date of Patent: Sep. 14, 2004

(54) STRAWBERRY PLANT NAMED 'DRISCOLL LANAI'

(50) Latin Name: *Fragaria×ananassa*
Varietal Denomination: Driscoll Lanai

(75) Inventors: Bruce D. Mowrey, Watsonville, CA (US); Larry T. Kodama, Salinas, CA (US); JoAnne Coss, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/722,055

(22) Filed: Nov. 25, 2003

(51) Int. Cl.[7] ..... A01H 5/00
(52) U.S. Cl. ..... Plt./209
(58) Field of Search ..... Plt./209

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll Lanai.' The variety is similar to the varieties 'San Juan', and 'Ana Maria'. The variety is distinguished from 'San Juan', and 'Ana Maria', in particular, by a bract frequency that is 80% typically paired, an orange-red external fruit color, an average of 300 achenes per fruit, a flat habit, dense stolon pubescence, a small size of calyx in relation to fruit on secondary fruit, a medium fruit flesh firmness, and moderately resistant to Verticillium wilt.

5 Drawing Sheets

Latin name of the genus and species of the plant claimed: The variety is botanically identified as *Fragaria×ananassa*.

1. BACKGROUND OF THE INVENTION

The new variety originated as a result of a controlled cross between the strawberry plants '62A313' (unpatented) and 'San Juan' (U.S. Plant Pat. No. 12,899) in an ongoing breeding program, and was discovered as a seedling in Monterey Country, Calif. in 1999. The original seedling of the new cultivar was asexually propagated by stolons in a Shasta County, Calif. Propagules were transplanted to a controlled breeding plot in Monterey Country, Calif., where the variety was identified and selected for further evaluation. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Driscoll Lanai'. The new variety is distinguished from other varieties by a number of characteristics as set forth in Tables 1–4.

3. COMPARISON TO SIMILAR VARIETIES

The varieties which we believe to be similar to 'Driscoll Lanai' from those known to us are 'San Juan' (U.S. Plant Pat. No. 12,899) and 'Ana Maria' (U.S. Plant Pat. No. 11,035). There are several characteristics of the new variety that are different from, or not possessed by 'San Juan' and 'Ana Maria'. The new variety is distinguished from 'San Juan' and 'Ana Maria' by having, for example, a bract frequency that is 80% typically paired, an orange-red external fruit color, an average of 300 achenes per fruit, a flat habit, dense stolon pubescence, a small size of calyx in relation to fruit on secondary fruit, a medium fruit flesh firmness, and moderately resistant to Verticillium wilt. Parent variety '62A313' was not available for side-by side comparison. 'Driscoll Lanai' differs from '62A313' by having better shipability and rounder berry shape. A comparison between 'Driscoll Lanai' and parent variety 'San Juan' can be found in Tables 1–4 below.

4. BRIEF DESCRIPTION OF THE DRAWINGS

The accompanying photographs show typical specimens of the new variety, including fruit, foliage, and flowers, in color as nearly true as it is reasonably possible to make in color illustrations of these characteristics.

5. DESCRIPTION OF THE NEW VARIETY

Figure 1:
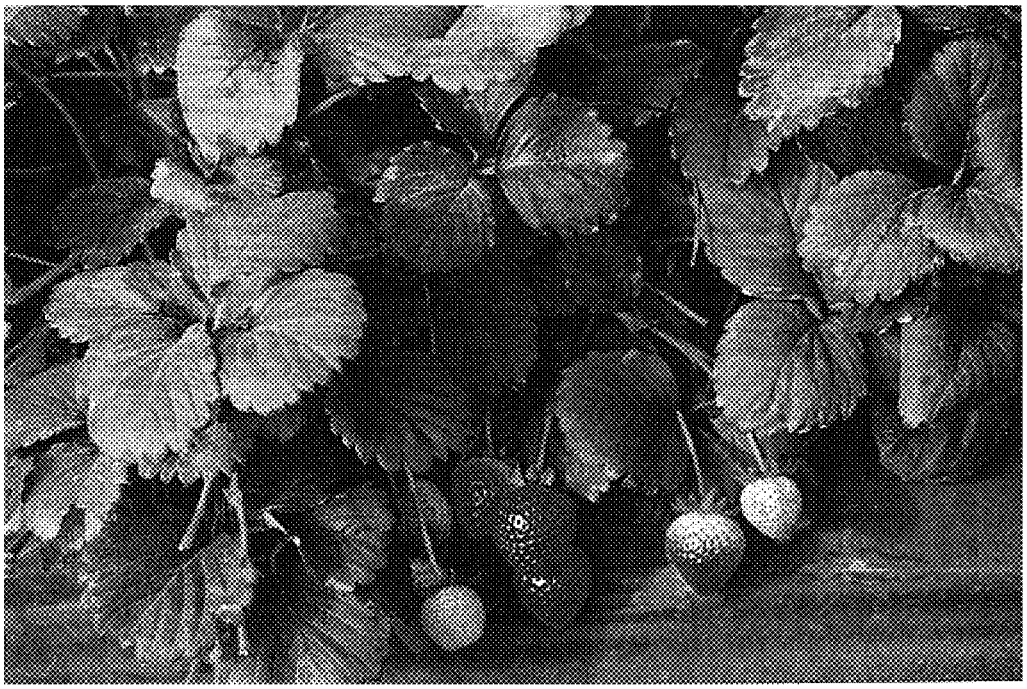
FIG. 1 shows the whole the plant.
Figure 2:
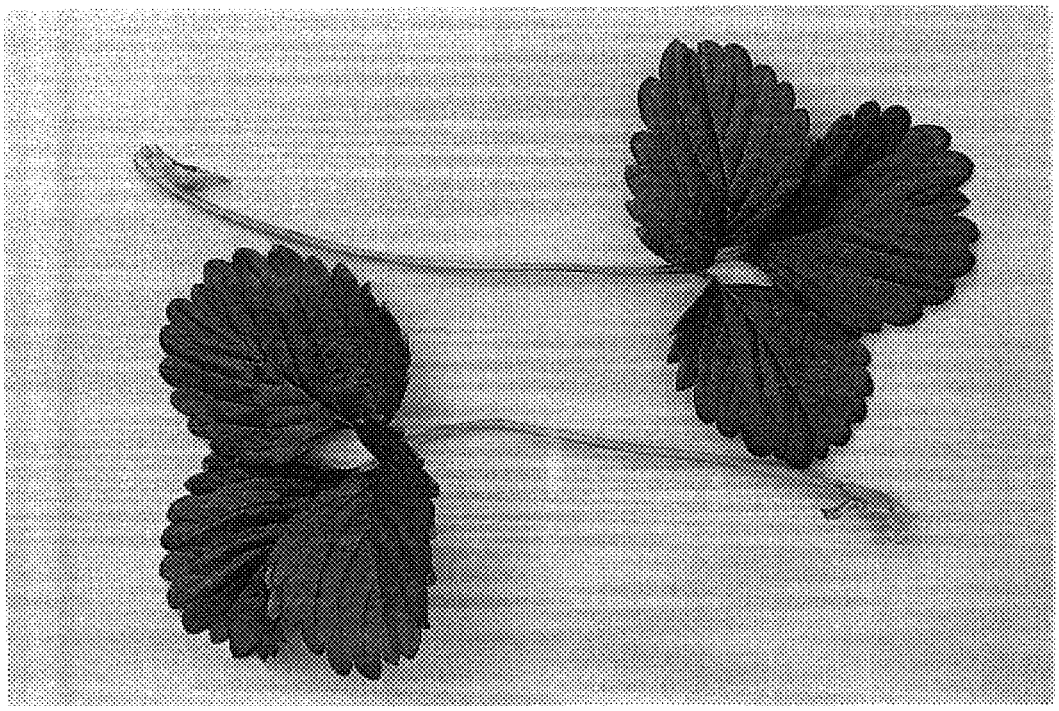
FIG. 2 shows the upper side of the leaves of the plant.
Figure 3:
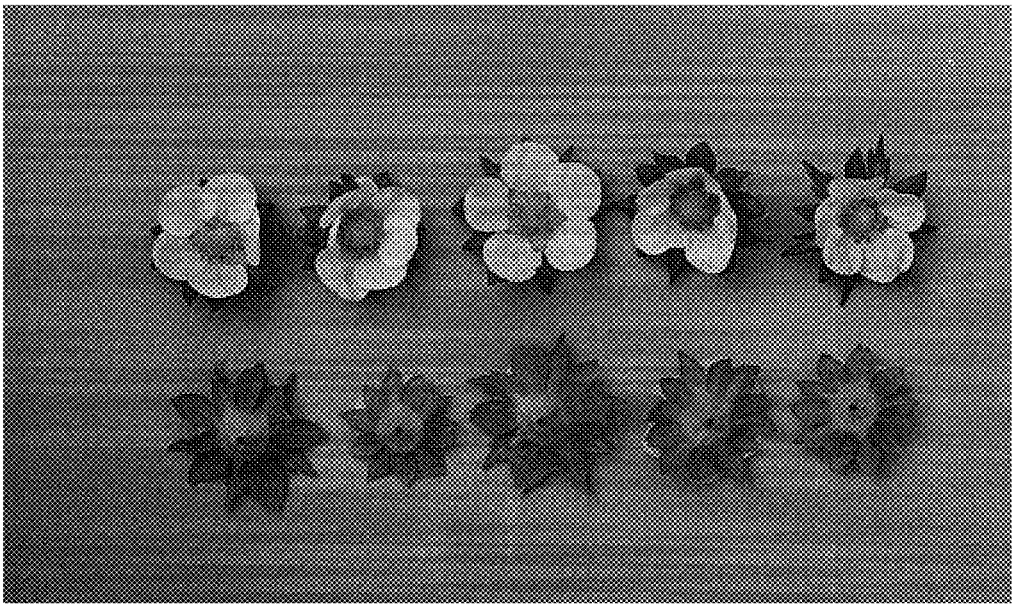
FIG. 3 shows the under side and upperside of the flowers.
Figure 4:
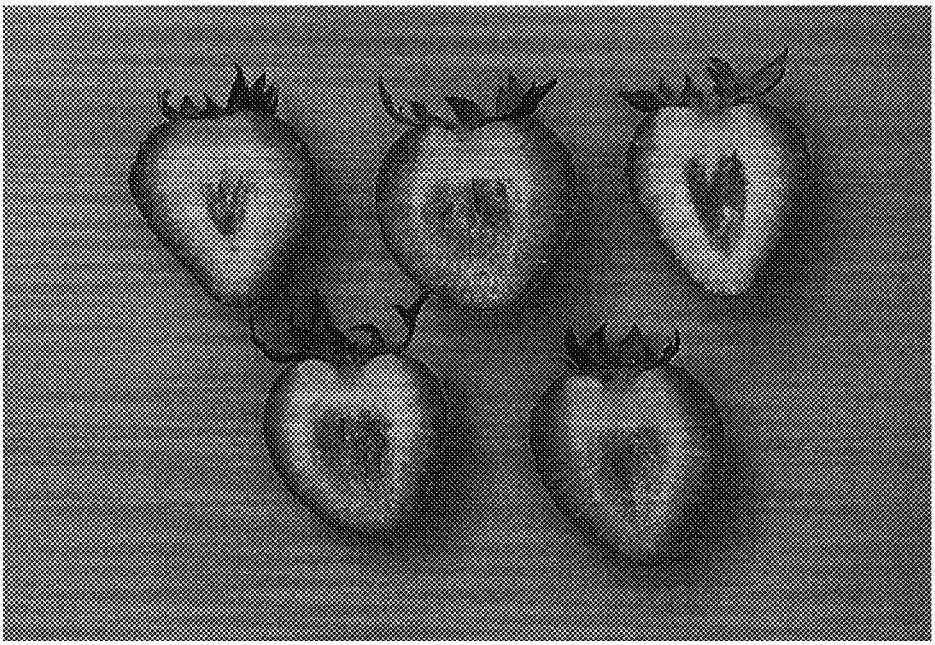
FIG. 4 shows the fruit in longitudinal cross-section.
Figure 5:
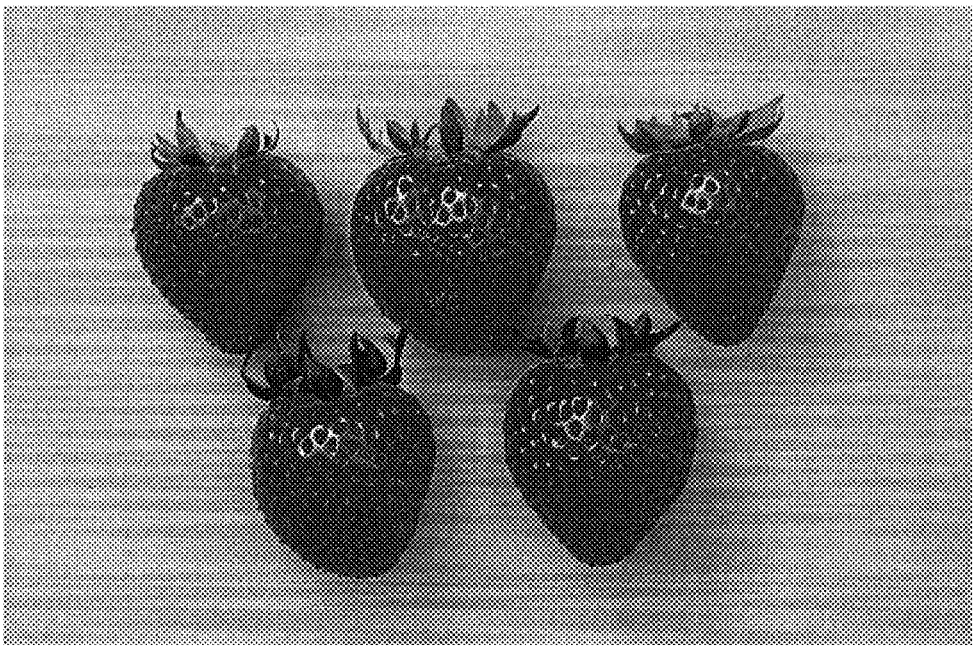
FIG. 5 shows a close-up of the fruit.

The following detailed description of the new variety is based upon observations taken of plants and fruit grown in Monterey County, Calif., U.S.A. This description is in accordance with UPOV terminology. Observations of 'Driscoll Lanai', 'San Juan', and 'Ana Maria' were taken in side-by-side comparison in 1999–2003. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.2 PROPAGATION

The new variety is principally propagated by way of stolons. Although propagation by stolons is presently preferred, other known methods of propagating strawberry plants may be employed.

5.3. CHARACTERISTICS OF THE NEW VARIETY

Information on the new variety is presented in Tables 1, 2, 3 and 4. In the tables, the flowers described are secondary flowers except where indicated. The fruit described is the secondary fruit on one-year-old plants. Fruit and flower measurements are an average of both primary and secondary fruit and flowers. Flowers of 'Driscoll Lanai' are fully self-fertile and typical of the species.

Table 1 provides information on the plant and fruit characteristics of the new variety 'Driscoll Lanai' compared with characteristics of 'San Juan' and 'Ana Maria'. Table 2 provides additional information of the plant and fruit characteristics of the new variety 'Driscoll Lanai' compared with characteristics of the varieties 'San Juan' and 'Ana Maria'. The information in the Tables for quantitative characteristics is shown in average values. Table 3 provides reactions of the new variety to pests and diseases compared with reactions of the varieties 'San Juan' and 'Ana Maria'. Table 4 provides isozyme characteristics of the new variety as compared to that of the varieties 'San Juan' and 'Ana Maria'.

TABLE 1

QUANTITATIVE COMPARISON OF 'DRISCOLL LANAI', 'SAN JUAN', AND 'ANA MARIA'

| | 'Driscoll Lanai' | 'Ana Maria' | 'San Juan' |
|---|---|---|---|
| Plant Characteristics | | | |
| Height of Plant (cm) | 21.9 | 27.4 | 22.1 |
| Spread of Plant (cm) | 47.6 | 52.4 | 47.6 |
| Number of Crowns | 5.3 | 4.8 | 3.7 |
| Leaf Characteristics | | | |
| Terminal Leaflet Length (cm) | 8.1 | 8.9 | 8.0 |
| Terminal Leaflet Width (cm) | 7.6 | 8.2 | 7.6 |
| Terminal Leaflet Length/Width Ratio | 1.07 | 1.09 | 1.06 |
| # Teeth/ Terminal Leaflet | 23.4 | 21.1 | 20 |
| Color of upper side | medium green 139A | medium green 147A | medium to dark green 147A |
| Color of under side | light green 138B | light green 148B | light green 147C |
| Petiole Length (cm) | 18.7 | 22.9 | 18.4 |
| Petiole Color | yellow-green 145A | yellow-green 145B | yellow-green 149A |
| Petiolule Length (mm) | 15.5 | 17.5 | 13.3 |
| Petiolule Diameter (mm) | 3.2 | 3.8 | 3.1 |
| Petiolule Color | yellow-green 145A | yellow-green 145B | yellow-green 149A |
| Bract Frequency | 80% typically paired | 20% typically single | 50% typically paired |
| Stipule Length (cm) | 3.7 | 3.2 | 3.2 |
| Stipule Width (cm) | 1.2 | 0.9 | 1.1 |

TABLE 1-continued

QUANTITATIVE COMPARISON OF 'DRISCOLL LANAI', 'SAN JUAN', AND 'ANA MARIA'

| | 'Driscoll Lanai' | 'Ana Maria' | 'San Juan' |
|---|---|---|---|
| Stolon Characteristics | | | |
| Anthocyanin Color | purple red 60A | | purple red 59A |
| Diameter at Bract (mm) | 3.74 | | 3.10 |
| Avg. # of Daughter Plants (2002 Nursery) | 67 | 52 | 57 |
| Flower Characteristics | | | |
| Petal Length (cm) | 1.21 | 1.23 | 1.04 |
| Petal Width (cm) | 1.29 | 1.20 | 1.07 |
| Petal Length/ Width Ratio | 0.94 | 1.03 | 0.97 |
| Flower Diameter (cm) | 2.58 | 2.64 | 2.3 |
| Calyx Diameter (cm) | 3.25 | 3.03 | 3.12 |
| Sepal Length (mm) | 14.80 | 11.90 | 11.97 |
| Sepal Width (cm) | 7.67 | 6.24 | 6.74 |
| Petal Color | white 155C | white 155D | white 155C |
| Fruiting Truss Length (cm) | 30.0 | 36.0 | 27.9 |
| Fruit Characteristics | | | |
| Fruit Length (cm) | 4.5 | 3.9 | 4.2 |
| Fruit Width (cm) | 3.8 | 3.6 | 4.0 |
| Fruit Length/ Width Ratio | 1.19 | 1.10 | 1.05 |
| Average Berry Weight (g) | 23.3 | 21.6 | 25.2 |
| External Color | orange red 45B | red 46A | dark red 53A |
| Internal Color | orange red 47C | orange red 44B | red 44A |
| Achene Coloration | gray-purple to yellow-green 185B to 154B | dark red to yellow 46B to 16A | dark red to yellow 46B to 16A |
| Achenes per Berry | 300 | 217 | 414 |
| Achene Weight (g) | .0059 | .0046 | .0051 |
| 2003 Yield (g/plant) | 1,679 | 1,645 | 1,449 |

TABLE 2

QUALITATIVE COMPARISON OF 'DRISCOLL LANAI', 'ANA MARIA' AND 'SAN JUAN'

| | 'Driscoll Lanai' | 'Ana Maria' | 'San Juan' |
|---|---|---|---|
| Plant | | | |
| Habit | flat | globose to upright | globose to flat globose |
| Canopy Density | open | medium to open | medium |
| Vigor | medium | strong | medium |
| Leaf | | | |
| Shape in Cross Section | slightly concave to flat | slightly concave to flat | flat to slightly convex |
| Interveinal Blistering | medium | medium to strong | medium to strong |
| Glossiness | weak | medium | weak to medium weak |
| Number of Leaflets | three only | three only | sometimes more than 3 leaflets (approx. 17% of leaves) |
| Terminal Leaflet Margin Profile | revolute to flat | flat | revolute to flat |
| Terminal Leaflet Shape of Base | rounded | rounded to oblique | obtuse to rounded |
| Terminal Leaflet Shape of Teeth | rounded | obtuse | rounded |
| Stipule Pubescence | medium to dense | sparse | medium |
| Petiole Pubescence | medium | sparse | medium |
| Petiole Pose of Hairs | downward | outward | outward to downward |
| Stolon | | | |
| Amount | many | medium to many | medium to many |
| Anthocyanin Coloration | strong | medium | strong |
| Thickness | medium to thick | thin to medium | medium |
| Pubescence | dense | sparse to medium | medium |
| Inflorescence | | | |
| Position Relative to Foliage | level to above | level to above | beneath to level with |
| Diameter of Calyx Relative to Corolla on Secondary Flowers | same size to larger | smaller to same size | larger |
| Diameter of Inner Calyx Relative to Outer on Secondary Flowers | larger | smaller to same size | same size |
| Spacing of Petals | overlapping | free to touching | overlapping |
| Fruiting Truss | | | |
| Attitude at First Picking | prostrate | semi-erect | prostrate |
| Fruit | | | |
| Predominant Shape | conical to ovoid | conical | conical to almost cylindrical |
| Difference in Shapes Between Primary and Secondary Fruits | slight | none to very slight | moderate |
| Band Without Achenes | narrow to medium | narrow to medium | narrow |
| Unevenness of Surface | weak | weak | medium |

TABLE 2-continued

QUALITATIVE COMPARISON OF 'DRISCOLL LANAI', 'ANA MARIA' AND 'SAN JUAN'

| | 'Driscoll Lanai' | 'Ana Maria' | 'San Juan' |
|---|---|---|---|
| Evenness of Color | even | even | even |
| Glossiness | strong | strong | very strong |
| Insertion of Achenes | level with surface | level with surface | level with surface |
| Insertion of Calyx | level | level with to set above | level |
| Pose of the Calyx Segments | spreading to reflexed | spreading | spreading to reflexed |
| Size of Calyx in Relation to Fruit, on Secondary Fruit | smaller | same size to larger | same size |
| Adherence of Calyx | strong | weak to medium | strong |
| Firmness of Flesh | medium | soft to medium | firm |
| Evenness of Flesh Color | uneven | slightly uneven | slightly uneven to even |
| Distribution of Flesh Color | marginal and central | marginal and central | marginal and central |
| Hollow Center Size | medium | small | medium |
| Sweetness | medium | medium to strong | medium to strong |
| Texture When Tasted | fine | fine to medium | medium |
| Acidity | medium | medium | medium |
| Time of Flowering | mid-February | early-February | mid-February |
| Harvest Interval in 2003 | late March thru early-November | mid-March thru early-November | late-March thru early-November |
| Type of Bearing | partially everbearing | partially everbearing | partially everbearing |

5.4. REACTION TO STRESS, PESTS, AND DISEASE

TABLE 3

REACTIONS TO STRESS PESTS AND DISEASES FOR 'DRISCOLL LANAI', 'SAN JUAN' AND 'ANA MARIA'

| | 'Driscoll Lanai' | 'Ana Maria' | 'San Juan' |
|---|---|---|---|
| Reaction to Pests | | | |
| *Tetranychus urticae* | susceptible | susceptible | moderately susceptible |
| *Lygus hesperus* | susceptible | susceptible | susceptible |
| Reaction To Diseases | | | |
| Botrytis Fruit Rot | susceptible | susceptible | susceptible |
| Powdery Mildew | susceptible | moderately susceptible | susceptible |
| Verticillium wilt | moderately resistant | susceptible | susceptible |
| Strawberry Mottle Virus | moderately resistant | moderately resistant | moderately resistant |
| *Xanthomonas fragariae* | moderately susceptible | moderately susceptible | moderately susceptible |

5.5. ISOZYME ANALYSIS

In addition to the morphological description above, the new cultivar 'Driscoll Lanai' has been analyzed to obtain an indication of its genetic makeup to provide further means for identifying the new variety and distinguishing it from other somewhat similar and/or related strawberry varieties. Specifically, leaf samples of 'Driscoll Lanai', 'San Juan', and 'Ana Maria' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL LANAI', 'ANA MARIA' AND 'SAN JUAN'

| Locus | 'DRISCOLL Lanai' | 'ANA MARIA' | 'SAN JUAN' |
|---|---|---|---|
| PGI | A1 | A1 | A2 |
| LAP | B3 | B3 | B3 |
| PGM | C2 | C4 | C4 |

What is claimed:

1. A new and distinct variety of strawberry plant, substantially as shown and described.

* * * * *